(12) United States Patent
Fernandez et al.

(10) Patent No.: US 7,691,103 B2
(45) Date of Patent: Apr. 6, 2010

(54) DEVICES FOR USE IN TRANSLUMINAL AND ENDOLUMINAL SURGERY

(75) Inventors: Raul Fernandez, Arlington, TX (US); Daniel J. Scott, Southlake, TX (US); Shou-Jiang Tang, Dallas, TX (US); Jeffrey A. Cadeddu, Dallas, TX (US); Richard A. Bergs, Rowlett, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/741,731

(22) Filed: Apr. 28, 2007

(65) Prior Publication Data
US 2007/0255273 A1    Nov. 1, 2007

Related U.S. Application Data

(60) Provisional application No. 60/795,923, filed on Apr. 29, 2006.

(51) Int. Cl.
*A61B 18/18* (2006.01)
(52) U.S. Cl. ........................................ 606/41; 607/101
(58) Field of Classification Search ............ 606/41–52; 414/1; 607/96, 98–102; 600/102
See application file for complete search history.

(56) References Cited

U.S. PATENT DOCUMENTS

| 3,043,309 | A | 7/1962 | McCarthy | 128/348 |
|---|---|---|---|---|
| 3,358,676 | A | 12/1967 | Frei et al. | 128/1.3 |
| 3,710,399 | A | 1/1973 | Hurst | 3/1 |
| 3,906,217 | A | 9/1975 | Lackore | 240/51.11 |
| 3,988,535 | A | 10/1976 | Hickman et al. | 178/6.8 |
| 4,047,136 | A | 9/1977 | Satto | 335/222 |
| 4,063,561 | A | 12/1977 | McKenna | 128/351 |
| 4,099,192 | A | 7/1978 | Aizawa et al. | 354/234 |
| 4,278,077 | A | 7/1981 | Mizumoto | 128/4 |
| 4,384,584 | A | 5/1983 | Chen | 604/28 |
| 4,585,282 | A | 4/1986 | Bosley | 308/10 |
| 4,597,390 | A * | 7/1986 | Mulhollan et al. | 606/148 |
| 4,655,746 | A | 4/1987 | Daniels et al. | 604/53 |

(Continued)

FOREIGN PATENT DOCUMENTS

WO    WO 2005/009211    2/2005

(Continued)

OTHER PUBLICATIONS

Office Action issued in U.S. Appl. No. 10/024,636, mailed Jul. 30, 2003.

(Continued)

*Primary Examiner*—Roy D Gibson
(74) *Attorney, Agent, or Firm*—Fulbright & Jaworski L.L.P.

(57) ABSTRACT

The present invention is a device and method of using a variety of laparoscopic or NOTES surgical tools at a confined or inaccessible space, e.g., an intra-abdominal surgical and NOTES tool inserted through a single incision through the skin or hollow viscus. Generally, the laparoscopic or NOTES surgical devices include a device body having a first side and a second side, wherein the first side includes a positioning mechanism and the second side includes one or more of a variety of laparoscopic or NOTES tools.

25 Claims, 8 Drawing Sheets

U.S. PATENT DOCUMENTS

| | | | |
|---|---|---|---|
| 4,671,287 A | 6/1987 | Fiddian-Green | 128/631 |
| 4,777,951 A | 10/1988 | Cribier et al. | 128/344 |
| 4,798,588 A | 1/1989 | Aillon | 604/122 |
| 4,803,506 A | 2/1989 | Diehl et al. | 354/400 |
| 4,910,633 A | 3/1990 | Quinn | 361/144 |
| 4,924,784 A | 5/1990 | Morishita et al. | 104/284 |
| 4,961,738 A | 10/1990 | Mackin | 606/15 |
| 4,967,670 A | 11/1990 | Morishita et al. | 104/284 |
| 5,007,919 A | 4/1991 | Silva et al. | 606/194 |
| 5,019,075 A | 5/1991 | Spears et al. | 606/7 |
| 5,093,754 A | 3/1992 | Kawashima | 361/144 |
| 5,099,216 A | 3/1992 | Pelrine | 335/220 |
| 5,150,272 A | 9/1992 | Danley et al. | 361/144 |
| 5,253,647 A | 10/1993 | Takahashi et al. | 128/653.1 |
| 5,267,091 A | 11/1993 | Chen | 359/872 |
| 5,324,260 A | 6/1994 | O'Neill et al. | 604/96 |
| 5,333,624 A | 8/1994 | Tovey | 128/897 |
| 5,352,219 A | 10/1994 | Reddy | 606/1 |
| 5,359,992 A | 11/1994 | Hori et al. | 128/4 |
| 5,370,640 A | 12/1994 | Kolff | 606/2 |
| 5,395,331 A | 3/1995 | O'Neill et al. | 604/96 |
| 5,409,483 A | 4/1995 | Campbell et al. | 606/15 |
| 5,431,640 A | 7/1995 | Gabriel | 604/270 |
| 5,445,615 A | 8/1995 | Yoon | 604/96 |
| 5,477,788 A | 12/1995 | Morishita | 104/284 |
| 5,489,256 A | 2/1996 | Adair | 600/133 |
| 5,540,648 A | 7/1996 | Yoon | 600/114 |
| 5,542,938 A | 8/1996 | Avellanet et al. | 604/280 |
| 5,562,657 A | 10/1996 | Griffin | 606/17 |
| 5,604,531 A | 2/1997 | Iddan et al. | 348/76 |
| 5,643,175 A | 7/1997 | Adair | 600/133 |
| 5,645,065 A | 7/1997 | Shapiro et al. | 128/653.1 |
| 5,653,677 A | 8/1997 | Okada et al. | 600/112 |
| 5,657,697 A | 8/1997 | Murai | 104/284 |
| 5,681,260 A | 10/1997 | Ueda et al. | 600/114 |
| 5,700,243 A | 12/1997 | Narciso, Jr. | 604/102 |
| 5,704,900 A | 1/1998 | Dobrovolny et al. | 600/229 |
| 5,722,326 A | 3/1998 | Post | 104/281 |
| 5,722,426 A | 3/1998 | Kolff | 128/898 |
| 5,732,636 A | 3/1998 | Wang et al. | 104/284 |
| 5,738,652 A | 4/1998 | Boyd et al. | 604/96 |
| 5,836,867 A | 11/1998 | Speier et al. | 600/112 |
| 5,883,454 A | 3/1999 | Hones et al. | 310/90.5 |
| 5,887,018 A | 3/1999 | Bayazitoglu et al. | 373/139 |
| 5,902,239 A | 5/1999 | Buurman | 600/427 |
| 5,904,147 A | 5/1999 | Conlan et al. | 128/899 |
| 5,906,579 A | 5/1999 | Salm et al. | 600/424 |
| 5,944,298 A | 8/1999 | Koike | 248/674 |
| 5,989,182 A | 11/1999 | Hori et al. | 600/112 |
| 6,007,484 A | 12/1999 | Thompson | 600/173 |
| 6,014,580 A | 1/2000 | Blume et al. | 600/424 |
| 6,123,466 A | 9/2000 | Persson et al. | 396/358 |
| 6,127,757 A | 10/2000 | Swinbanks | 310/90.5 |
| 6,173,199 B1 | 1/2001 | Gabriel | 600/424 |
| 6,173,715 B1 | 1/2001 | Sinanan et al. | 128/899 |
| 6,219,572 B1 | 4/2001 | Young | 600/431 |
| 6,233,476 B1 | 5/2001 | Strommer et al. | 600/424 |
| 6,248,074 B1 | 6/2001 | Ohno et al. | 600/463 |
| 6,315,789 B1 | 11/2001 | Cragg | 606/232 |
| 6,371,952 B1 | 4/2002 | Madhani et al. | 606/1 |
| 6,471,172 B1 | 10/2002 | Lemke et al. | 248/278.1 |
| 6,522,909 B1 | 2/2003 | Garibaldi et al. | 600/424 |
| 6,524,283 B1 | 2/2003 | Hopper et al. | 604/264 |
| 6,535,764 B2 | 3/2003 | Imran et al. | 607/40 |
| 6,537,196 B1 | 3/2003 | Creighton et al. | 600/12 |
| 6,540,693 B2 | 4/2003 | Burbank et al. | 600/564 |
| 6,594,517 B1 | 7/2003 | Nevo | 600/411 |
| 6,648,817 B2 | 11/2003 | Schara et al. | 600/173 |
| 6,656,194 B1 | 12/2003 | Gannoe et al. | 606/153 |
| 6,719,684 B2 | 4/2004 | Kim et al. | 600/101 |
| 6,776,165 B2 | 8/2004 | Jin | 128/899 |
| 6,936,003 B2 | 8/2005 | Iddan | 600/114 |
| 6,974,462 B2 | 12/2005 | Sater | 606/72 |
| 6,986,738 B2 | 1/2006 | Glukhovsky | 600/109 |
| 7,039,453 B2 | 5/2006 | Mullick et al. | 600/476 |
| 7,042,184 B2 | 5/2006 | Oleynikov et al. | 318/568.12 |
| 7,066,879 B2 * | 6/2006 | Fowler et al. | 600/102 |
| 7,083,579 B2 | 8/2006 | Yokoi et al. | 600/593 |
| 7,083,617 B2 * | 8/2006 | Kortenbach et al. | 606/46 |
| 7,096,560 B2 | 8/2006 | Oddsen, Jr. | 29/525.11 |
| 7,120,498 B2 | 10/2006 | Imran et al. | 607/40 |
| 7,169,104 B2 | 1/2007 | Ueda et al. | 600/568.12 |
| 7,199,545 B2 | 4/2007 | Oleynikov et al. | 318/568.12 |
| 7,211,094 B2 | 5/2007 | Gannoe et al. | 606/151 |
| 7,235,064 B2 | 6/2007 | Hopper et al. | 606/167 |
| 7,241,290 B2 | 7/2007 | Doyle et al. | 606/1 |
| 7,276,065 B2 * | 10/2007 | Morley et al. | 606/41 |
| 7,429,259 B2 | 9/2008 | Cadeddu et al. | 606/1 |
| 7,448,993 B2 | 11/2008 | Yokoi et al. | 600/114 |
| 2001/0051766 A1 | 12/2001 | Gazdzinski | 600/109 |
| 2002/0095175 A1 | 7/2002 | Brock et al. | 606/205 |
| 2003/0060702 A1 | 3/2003 | Kuth et al. | 600/424 |
| 2003/0066938 A1 | 4/2003 | Zimmerman | 248/301 |
| 2003/0114731 A1 | 6/2003 | Cadeddu | 600/146 |
| 2004/0093039 A1 | 5/2004 | Schumert | 607/40 |
| 2004/0133089 A1 | 7/2004 | Kilcoyne | 600/300 |
| 2005/0119640 A1 | 6/2005 | Sverduk et al. | 606/1 |
| 2005/0165449 A1 | 7/2005 | Cadeddu et al. | |
| 2005/0215858 A1 | 9/2005 | Vail | 600/135 |
| 2005/0272972 A1 | 12/2005 | Iddan | 600/565 |
| 2005/0272974 A1 | 12/2005 | Iddan | 600/114 |
| 2005/0273139 A1 | 12/2005 | Krauss et al. | 606/142 |
| 2005/0288555 A1 | 12/2005 | Binmoeller | 600/112 |
| 2006/0149135 A1 | 7/2006 | Paz | 600/201 |
| 2006/0195015 A1 | 8/2006 | Mullick et al. | 600/407 |
| 2006/0229592 A1 | 10/2006 | Yokoi et al. | 600/593 |
| 2007/0010709 A1 | 1/2007 | Reinschke | 600/156 |
| 2007/0020065 A1 * | 1/2007 | Kirby | 414/1 |
| 2007/0032700 A1 | 2/2007 | Fowler et al. | 600/102 |
| 2007/0032701 A1 | 2/2007 | Fowler et al. | 600/102 |
| 2007/0051766 A1 | 3/2007 | Spencer | 224/605 |
| 2007/0123748 A1 | 5/2007 | Meglan | 606/10 |
| 2007/0156015 A1 | 7/2007 | Gilad | 600/101 |
| 2007/0255100 A1 | 11/2007 | Barlow et al. | 600/114 |
| 2007/0270651 A1 | 11/2007 | Gilad et al. | 606/144 |
| 2008/0015413 A1 | 1/2008 | Barlow et al. | 600/114 |
| 2008/0015552 A1 | 1/2008 | Doyle et al. | 606/100 |
| 2008/0269779 A1 | 10/2008 | Cadeddu et al. | 606/130 |

FOREIGN PATENT DOCUMENTS

WO WO 2007/063550 6/2007

OTHER PUBLICATIONS

Office Action issued in U.S. Appl. No. 10/999,396, mailed Apr. 13, 2007.

Office Action issued in U.S. Appl. No. 10/999,396, mailed Aug. 29, 2007.

Office Action issued in U.S. Appl. No. 10/999,396, mailed Oct. 16, 2006.

Cadeddu et al., "Magnetic positioning system for trocarless laparoscopic instruments," *American College of Surgeons Poster*, 2004.

Cadeddu et al., "Novel magnetically guided intra-abdominal camera to facilitate laparoendoscopic single site surgery: initial human experience," *Surgical Endoscopy*, SAGES Oral Manuscript, 2009.

Cadeddu et al., "Transabdominal magnetic anchoring system for trocar-less laparoscopic surgery," *American Urological Association Poster*, 2002.

Cadeddu et al., "Transabdominal magnetic anchoring system for trocar-less laparoscopic surgery," *Journal of Urology Abstract*, 2002.

Castellvi et al., "Completely transvaginal NOTES cholecystectomy in a porcine model using novel endoscopic instrumentation," *Accepted for Poster Presentation*, SAGES Annual Meeting, 2009.

Castellvi et al., "Hybrid transgastric NOTES cholecystectomy in a porcine model using a magnetically anchored cautery and novel instrumentation," *Submitted for Presentation, ASGE*, 2009.

Castellvi et al., "Hybrid transvaginal NOTES sleeve gastrectomy in a porcine model using a magnetically anchored camera and novel instrumentation," *Accepted for Poster Presentation, SAGES Annual Meeting*, 2009.

Duchene et al., "Magnetic positioning system for trocarless laparoscopic instruments," *Engineering and Urology Society Poster*, 2004.

Fernandez et al., "Development of a transabdominal anchoring system for trocar-less laparoscopic surgery," *ASME Proceedings of IMECE*, 2003.

Gedeon et al., "Maximizing coupling strength of magnetically anchored notes instruments: How thick can we go?" *Submitted for Presentation, SAGES Annual Meeting*, 2008.

Gedeon et al., "Maximizing coupling strength of magnetically anchored notes instruments: How thick can we go?" *SAGES Annual Meeting Poster*, 2008.

Park et al., "Trocar-less instrumentation for laparoscopy," *Annals of Surgery*, 245(3):379-384, 2007.

Raman et al., "Complete transvaginal NOTES nephrectomy using magnetically anchored instrumentation," *Journal of Endourology*, 23(3):, 2009.367-371, 2009.

Scott et al., "A randomized comparison of laparoscopic, flexible endoscopic, and wired and wireless magnetic NOTES cameras on ex-vivo and in-vivo surgical performance," *Digestive Disease Week (DDW), American Society for Gastrointestinal Endoscopy (ASGE) Annual Meeting Abstract*, 2008.

Scott et al., "A randomized comparison of laparoscopic, flexible endoscopic, and wired and wireless magnetic NOTES cameras on ex-vivo and in-vivo surgical performance," *Digestive Disease Week (DDW), American Society for Gastrointestinal Endoscopy (ASGE) Annual Meeting Poster*, 2008.

Scott et al., "Completely transvaginal cholecystectomy using magnetically anchored instruments," *Plenary Oral Presentation, SAGES Annual Meeting*, 2007.

Scott et al., "Completely transvaginal NOTES cholecystectomy using magnetically anchored instruments," *Surg. Endosc.*, 21:2308-2316, 2007.

Scott et al., "Evaluation of a novel air seal access port for transvaginal notes cholecystectomy," *Submitted for Presentation, SAGES Annual Meeting*, 2008.

Scott et al., "Evaluation of a novel air seal access port for transvaginal notes cholecystectomy," *SAGES Annual Meeting Poster*, 2008.

Scott et al., "Magnetically anchored instruments for transgastric endoscopic surgery," *Oral Presentation for SAGES Annual Meeting, Emerging Technology Oral Abstract ET005*, 2006.

Scott et al., "Magnetically anchored instruments for transgastric endoscopic surgery," *SAGES Presentation*, 2006.

Scott et al., "Optimizing magnetically anchored camera, light source, graspers, and cautery dissector for transvaginal notes cholecystectomy," *Submitted for Presentation, SAGES Annual Meeting*, 2008.

Scott et al., "Optimizing magnetically anchored camera, light source, graspers, and cautery dissector for transvaginal notes cholecystectomy," *SAGES Annual Meeting Poster*, 2008.

Scott et al., "Short-term survival outcomes following transvaginal NOTES cholecystectomy using magnetically anchored instruments," *Submitted for Oral or Poster Presentation, SAGES Annual Meeting*, 2007.

Scott et al., "Short-term survival outcomes following transvaginal NOTES cholecystectomy using magnetically anchored instruments," *ACS Presentation*, 2007.

Scott et al., "Short-term survival outcomes following transvaginal NOTES cholecystectomy using magnetically anchored instruments," *Oral Presentation, ASGE Annual Meeting/DDW*, 2007.

Scott et al., "Transgastric, transcolonic, and transvaginal cholecystectomy using magnetically anchored instruments," *Submitted for Poster Presentation, ACS Annual Meeting*, 2007.

Scott et al., "Transgastric, transcolonic, and transvaginal cholecystectomy using magnetically anchored instruments," *ACS Poster*, 2007.

Scott et al., "Transgastric, transcolonic, and transvaginal cholecystectomy using magnetically anchored instruments," *Poster Presentation, SAGES Annual Meeting*, 2007.

Scott et al., "Transgastric, transcolonic, and transvaginal cholecystectomy using magnetically anchored instruments," *SAGES Annual Meeting Poster*, 2007.

Scott et al., "Transvaginal NOTES cholecystectomy using magnetically anchored instruments," *Abstract for Video Submission, ASGE 11th Annual Video Forum*, 2007.

Scott et al., "Transvaginal single access 'pure' NOTES sleeve gastrectomy using a deployable magnetically anchored video camera," *Digestive Disease Week (DDW), American Society for Gastrointestinal Endoscopy (ASGE) Annual Meeting Abstract*, 2008.

Scott et al., "Transvaginal single access 'pure' NOTES sleeve gastrectomy using a deployable magnetically anchored video camera," *Digestive Disease Week (DDW), American Society for Gastrointestinal Endoscopy (ASGE) Annual Meeting Poster*, 2008.

Swain et al., "Linear stapler formation of ileo-rectal, entero-enteral and gastrojejunal anastomoses during dual and single access 'pure' NOTES procedures: Methods, magnets and stapler modifications," *Digestive Disease Week (DDW), American Society for Gastrointestinal Endoscopy (ASGE) Annual Meeting Abstract*, 2008.

Swain et al., "Linear stapler formation of ileo-rectal, entero-enteral and gastrojejunal anastomoses during dual and single access 'pure' NOTES procedures: Methods, magnets and stapler modifications," *Digestive Disease Week (DDW), American Society for Gastrointestinal Endoscopy (ASGE) Annual Meeting Poster*, 2008.

Swain et al., "Wireless endosurgery for NOTES," *Digestive Disease Week (DDW), American Society for Gastrointestinal Endoscopy (ASGE) Annual Meeting Abstract*, 2008.

Tang et al., "Live video manipulator for endoscopy and natural orifice transluminal endoscopic surgery (with videos)," *Gastrointestinal Endoscopy*, 68:559-564, 2008.

Tang et al., "Live video manipulator for endoscopy and NOTES (with videos)," *American Society for Gastrointestinal Endoscopy (ASGE) Annual Meeting Abstract*, 2008.

Zeltser et al., "Single trocar laparoscopic nephrectomy using magnetic anchoring and guidance system in the porcine model," *The Journal of Urology*, 178:288-291, 2007.

\* cited by examiner

DEVICES FOR USE IN TRANSLUMINAL AND ENDOLUMINAL SURGERY

CROSS-REFERENCE TO RELATED APPLICATIONS

This application claims priority to U.S. Provisional Patent Application No. 60/795,923, filed Apr. 29, 2006, the entire contents of which are incorporated herein by reference. This application is related to U.S. patent application Ser. No. 10/999,396, filed Nov. 30, 2004, incorporated herein by reference in its entirety, now U.S. Pat. No. 7,429,259, and U.S patent application Ser. No. 12/146,953, filed Jun. 26, 2008, which is a Continuation of application Ser. No. 10/999,396.

TECHNICAL FIELD OF THE INVENTION

The present invention relates to an apparatus and system for performing surgery, and in particular, to tools for hands-free operation and control of medical instruments inside a body cavity.

BACKGROUND OF THE INVENTION

Without limiting the scope of the invention, its background is described with respect to surgical procedures, and in particular, laparoscopy and transmural and endoluminal surgery, e.g., Natural Orifice Transluminal Endoscopic Surgery (NOTES).

Compared with open surgery, laparoscopy results in significantly less pain, faster convalescence and less morbidity. NOTES, an even less invasive surgical approach, is likely to achieve similar results. However, eye-hand dissociation, a two-dimensional field-of-view and instrumentation with limited degrees of freedom contribute to a steep learning curve and demanding dexterity requirements for many laparoscopic and endoscopic procedures. One of the main limitations of laparoscopy is the fixed working envelope surrounding each trocar, often necessitating placement of multiple ports to accommodate changes in position of the instruments or laparoscope to improve visibility and efficiency. The placement of additional working ports contributes to post-operative pain and carries a small risk of bleeding or adjacent organ damage.

SUMMARY OF THE INVENTION

The present inventors recognized the need for a system that reduces the required number of ports of entry during surgery. For endoscopic and NOTES procedures, only one or two accessory instruments can be passed through the endoscopic channel. In addition, the flexible endoscope can not provide desired stiffness when needed. What is needed is a system that provides additional tools, increased strength and different directional mechanical force.

In order to provide for greater flexibility in instrument usage and to further reduce morbidity, an anchor system and surgical devices or tools that can be used in laparoscopic surgery and NOTES have been developed around an internally positioned surgical device. The various devices are capable of various laparoscopic and NOTES functions and may be secured to the abdominal wall or hollow viscus via magnetic coupling, suction, mechanical fixation or attached to other devices. For example, the devices and tools of the present invention may be secured via a detachable pin or needle that crosses into the body cavity and leaves, at most, a very small puncture wound. In addition, the laparoscopic surgical and NOTES device may include a connection for device removal, electrical power, mechanical power, pneumatic power, optical viewing, lighting and other power. In addition, the laparoscopic surgical and NOTES devices of the present invention may be supported externally to the surgical device located internally. More particularly, the present invention includes a device for manipulating a surgical tool at an intended manipulation location within the body and cavities.

The present invention includes a variety of laparoscopic surgical and NOTES devices that perform numerous functions. For example, the present invention includes a variety of tissue and/or organ retractors or clamps, e.g., a suction cup with detachable suction tubing, an activatable clamp or jaw mechanism, a pin or other device to pierces and/or transfix the tissue, an anchoring system that is deployed within the targeted tissue, a T-fastener, a cross, a ring or an inflatable balloon configuration, a suturing type of surgical tool and a clipping type of surgical tool. Additionally, the surgical device may be a camera, a retractor, a clamp, a paddle, a hose, a cutting tool, a light, a hook, a net or an attachment point to the surgical anchor. The laparoscopic surgical and NOTES device may also include a drawstring for removal.

The present invention provides a laparoscopic surgical and NOTES electro-cautery device having a device body with a first side and a second side. The first side includes an anchoring and positioning mechanism and the second side includes an electro-cautery surgical mechanism.

The present invention also provides a laparoscopic surgical and NOTES retention device having a top surface and a bottom surface. The top surface includes an anchoring and positioning mechanism and the bottom surface includes a retention device having one or more movable members used to grasp an item, object, tool, blood vessel or organ.

A laparoscopic and NOTES device is also provided that includes a top surface and a bottom surface, with the top surface having an anchoring and positioning mechanism and the bottom surface having a needle with a lumen. The needle is positioned in a needle driving device that provides a force to extend the needle and position the needle.

The present invention also includes a laparoscopic surgical and NOTES vacuum cup device having a top surface with an anchoring and positioning mechanism and a bottom surface with a vacuum cup. The vacuum cup is located on or about a telescopic arm or structure connected to a vacuum cup.

The laparoscopic surgical and NOTES device of the present invention may include ferrous material disposed on, in or about the surgical anchoring and positioning mechanism, or it may even be a wire, wires, a wire bundle and the like and may be, e.g., oriented along the length of the surgical and NOTES anchor in one or more orientations. The ferrous material of the laparoscopic surgical and NOTES device may be used to attract a magnet positioned externally from the body cavity and hollow viscus, wherein manipulation of the magnet directs movement of the laparoscopic surgical and NOTES device within the body cavity or vice versa, that is, the surgical anchoring and positioning mechanism is magnetic and a ferrous material or another magnet is external to the body cavity and hollow viscus. In one embodiment, the magnet is, e.g., a permanent magnet.

The laparoscopic surgical and NOTES device may further include a ferrous insert, coating or combination thereof that permits manipulation (position and orientation) of the laparoscopic surgical and NOTES device after insertion without the need for permanent tools or connections. The laparoscopic surgical and NOTES device may also include magnets or suction cups that increase the control for positioning and strengthening the attachment in a hands-free system, which may be further augmented by mechanical attachment, e.g., using a locking, detachable pin. One such pin-anchored system has been developed by the present inventors as taught in U.S. Patent Application US20050165449A1, relevant portions incorporated herein by reference. After insertion into, e.g., an abdominal cavity and hollow viscus, the surgical and NOTES anchor and tools attached thereto remain surgeon-controlled via, e.g., external magnetic couples on the patient's abdomen and outside the hollow viscus. Using the surgical and NOTES system disclosed herein, instruments, e.g., miniature endoscopic cameras, lights, retractors, scalpels, clamps and the like may be used to augment, e.g., the surgical field of view, surgical precision and anchoring.

Accordingly, the present inventors have recognized that the field of laparoscopic surgery and NOTES needs a method and apparatus that enables a surgeon or an endoscopist to manipulate the position and orientation of one or more instruments within a human body and hollow viscus without the necessity for multiple entry points, trocars, or endoscopes. To provide for greater flexibility of endoscopic viewing and instrument usage and to further reduce morbidity, the inventors have developed a novel laparoscopic and NOTES system that allows for unrestricted intra-abdominal and intraluminal movement of an endoscopic camera and instruments without additional port sites and endoscopes.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

DETAILED DESCRIPTION OF THE INVENTION

Figure 1:
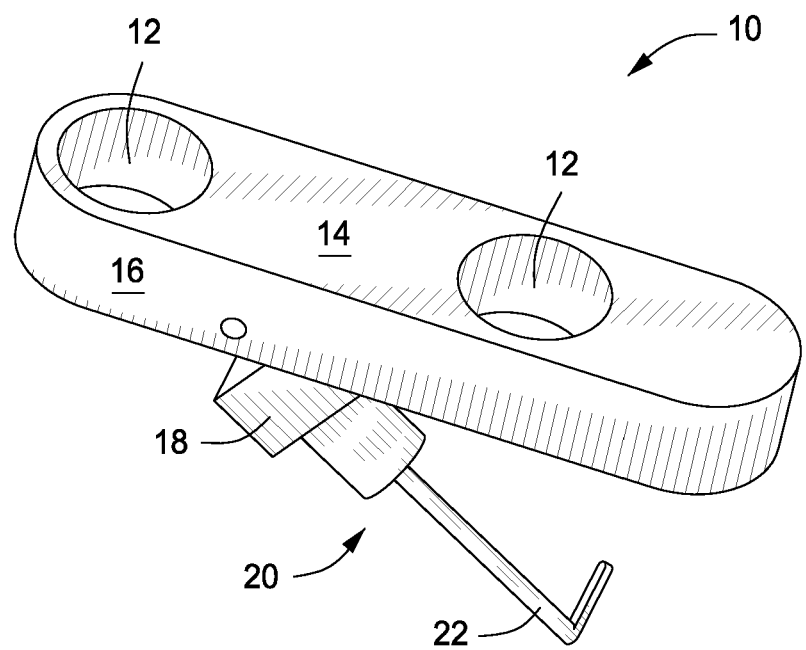
FIG. 1 is an isometric view of the laparoscopic and NOTES electro-cautery surgical device of the present invention.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

A general description of laparoscopic surgery and NOTES is set forth herein to demonstrate the use of the present invention in one type of surgery and is not intended to be exhaustive or to limit the scope of the invention. The present invention may include modifications and variations of each are possible in light of the teachings described herein without departing from the spirit and scope of the following claims. It is contemplated that the use of the present invention can involve components having different characteristics. It is intended that the scope of the present invention be defined by the claims appended hereto, giving full cognizance to equivalents in all respects.

As used herein, a "laparoscopic" device refers to any type of surgical tool that has been reduced in size for entry into a body cavity or organ. Non-limiting examples of tools that are attached to, or form part of, a laparoscopic device include a camera, a retractor, a clamp, a paddle, a hose, a cutting tool, a light, a hook, a net and an anchor having attachment points. Other examples include tissue and/or organ retractors or clamps, e.g., a suction cup with detachable suction tubing; an activatable clamp; a needle or other device to pierces or transfix a tissue; an anchoring system that is deployed within the targeted tissue, e.g., a T-fastener, a cross, a ring or an inflatable balloon configuration; a suturing, staple or clipping type of surgical tool.

As used herein, a "Natural orifice transluminal endoscopic surgery (NOTES)" device refers specifically to any type of tools and devices that are used to assist and perform transmural or endoluminal surgery. Non-limiting examples of tools that are attached to, or form part of, a NOTES device include a camera, a retractor, a clamp, a cutting tool, a light, a hook, a net, and an anchor having attachment points. Other examples include tissue and/or organ retractors or clamps, e.g., a suction cup with detachable suction tubing; an activatable clamp; a needle or other device to pierces or transfix a tissue; an anchoring system that is deployed within the targeted tissue, e.g., a T-fastener, a cross, a ring or an inflatable balloon configuration; a suturing, staple or clipping type of NOTES tool.

The laparoscopic or NOTES devices may be provided as part of a surgical trocar most commonly used in laparoscopic, transluminal and/or endoscopic surgery. For example, prior to use of the trocar, the surgeon may introduce a Veress needle into the patient's abdominal cavity. The Veress needle has a stylet, which permits the introduction of gas into the abdominal cavity. After the Veress needle is properly inserted, it is connected to a gas source and the abdominal cavity is insufflated to an approximate abdominal pressure of, e.g., 15 mm Hg. By insufflating the abdominal cavity, pneumoperitoneum is created separating the wall of the body cavity from the internal organs.

A trocar with a piercing tip is then used to puncture the body cavity. The piercing tip or obturator of the trocar is inserted through the cannula or sheath and the cannula partially enters the body cavity through the incision made by the trocar. The obturator may then be removed from the cannula and an elongated endoscope or camera may be inserted through the cannula to view the body cavity, or surgical instruments may be inserted to perform ligations or other procedures.

A great deal of force is often required to cause the obturator to pierce the wall of the body cavity. When the piercing tip breaks through the cavity wall, resistance to penetration ceases and the tip may reach internal organs or blood vessels, with resultant lacerations and potentially serious injury. The creation of the pneumoperitoneum provides some free space within which the surgeon may stop the penetration of the trocar. To provide further protection, trocars have more recently been developed with spring-loaded shields surrounding the piercing tip of the obturator. Once the piercing tip of the obturator has completely pierced the body cavity wall, the resistance of the tissue to the spring-loaded shield is reduced and the shield springs forward into the body cavity and covers the piercing tip. The shield thereby protects internal body organs and blood vessels from incidental contact with the piercing tip and resultant injury.

Once the cannula has been introduced into the opening in the body cavity wall, the pneumoperitoneum may be maintained by introducing gas into the abdominal cavity through the cannula. Various seals and valves have been used to allow abdominal pressure to be maintained in this fashion. Maintaining abdominal pressure is important both to allow working room in the body cavity for instruments introduced through the cannula and to provide free space for the puncturing of the body cavity wall by one or more additional trocars as may be required for some procedures.

A principal limitation of traditional laparoscopy relates to the fixed working envelope surrounding each trocar. These relatively small working envelopes often necessitate the placement of multiple ports in order to accommodate necessary changes in instrument position and to improve visibility and efficiency. The creation of additional ports is known to contribute to post-operative pain and to increase the risk of bleeding or organ damage. Therefore, the present invention has been developed to: (1) improve the control of tools within a surgical envelope; (2) reduce the number of trocars required (e.g., a single puncture); (3) improve the working envelope associated with, e.g., laparoscopic surgery; and/or (4) improve instrument positioning, visibility and efficiency.

For NOTES, the insufflation medium is introduced into the hollow viscus and body cavity through an endoscope or an overtube. Principal limitations of traditional endoscopy relate to the limited numbers of instruments that can be passed through the endoscopic accessory channel, the lack of trangulation, the lack of visual depth, the lack of different directional force and the lack of desired stiffness of the endoscope when needed. Therefore, the present invention has been developed to: (1) improve the control of tools within a NOTES platform; (2) increase the number of accessory and tools; (3) improve the working envelope associated with, e.g., NOTES; (4) improve instrument positioning, visibility and efficiency; (5) provide trangulation and different directional force.

The present invention includes laparoscopic and NOTES surgical devices that may be secured to the abdominal wall and hollow viscus and subsequently positioned using surgeon-controlled magnetic couplers on the patient's abdomen and hollow viscus. Using the laparoscopic and NOTES surgical devices disclosed herein, in conjunction with the techniques outlined for magnetic manipulation, laparoscopic and NOTES surgical devices may be used to augment, aid and perform specific tasks or procedures. The present inventors have evaluated the theoretical and empirical uses of the laparoscopic and NOTES surgical devices and optimized for size, strength and surgical compatibility, as well as the benefits, limitations and prospects for the use of incisionless, laparoscopic and NOTES surgical devices in laparoscopic and NOTES surgery. In one example, the laparoscopic and NOTES surgical devices of the present invention will find particular use in single trocar and single-incision surgery, which may include transmural delivery that eliminates incisions on the skin. In another example, the present invention permits incisions in surfaces with low visibility and delivery of the laparoscopic and NOTES surgical device or surgical tools to the location of the surgery, e.g., trans-umbilical.

Several types and generations of magnetic anchoring schemes and laparoscopic and NOTES surgical devices have been developed and evaluated. A fundamental design decision arises in generating the magnetic field electrically or via permanently magnetized materials. Electromagnets were initially favored due to: (1) the intrinsic ability to control the field strength, from zero to a maximum desired value; and (2) high magnetizing forces available in a relatively small footprint. Ex vivo and in vivo studies were used to evaluate the attractive force needed for use of electromagnets and permanent magnets. With electromagnets it was found that field strength was high at direct contact with the core, however, the field strength across tissue dropped-off drastically over relatively short distances, resulting in relatively bulky and heavy devices even after optimizing their length-to-diameter ratio and winding configuration. It was also found that heating caused by resistance limited the useful force attainable from an electromagnet due to its effect on skin contact temperature, winding insulation integrity, and surgeon comfort; these drawbacks may be overcome with active cooling. Given these constraints, permanent magnets were also investigated and were found to deliver a higher coupling force per unit volume than the basic electromagnetic designs, and can be controlled, when required, by adjusting their distance from their magnetic couple manually or in a closed-loop system. One limitation of permanent magnets relative to electromagnets is that the coupling force is always present, causing attraction to unintended targets and thus requiring strict handling procedures in the operating room. As such, in some applications electromagnets may be preferred, while in others permanent magnets may be preferred.

Magnetic performance is the result of complex, three-dimensional field interactions governed by material, size, shape, location of magnetic poles and location relative to the target. For this reason, practical design analyses and optimization are tractable only through computer simulation and empirical testing. In arriving at an optimal magnetic anchoring system configuration, the main constraint is the size of the intraabdominal couple, which must be designed to fit through the laparoscopic or NOTES delivery port. The dimensions of the external anchor are not critical but must be kept as small as practical and ergonomically compatible with abdominal laparoscopic and NOTES surgery.

In one non-limiting example, the device has a sufficient coupling force, nominally higher than about 500 grams at a 10 mm gap. The skilled artisan will recognize that the coupling force may be varied depending on tissue type and thickness, the weight of the device, device material and device size. In certain examples, two different magnetic anchoring systems have bee developed. For example, one device used was based on a ø9×12 mm internal magnet coupled to a ø25×50 mm external magnet in single-stack and double stack (side-by-side, 25 mm between centerlines) configurations; all use NdFeB rare-earth magnets. The size, mechanical strength and control of these devices may be varied by adding other mechanical or physical control parameters, e.g. pins, suction, graspers, hook-and-loop fasteners and the like.

A wide variety of permanent magnets may be used with the present invention, such as rare earth magnets, ceramic magnets, alnico magnets, which may be rigid, semi-rigid or flexible. Flexible magnets are made by impregnating a flexible material such as neoprene rubber, vinyl, nitrile, nylon or a plastic with a material such as iron having magnetic characteristics. Other examples of magnets for use as described hereinabove, include rare earth magnets, e.g., neodymium iron boron (NdFeB) and Samarium Cobalt (SmCo) classes of magnets. Within each of these classes are a number of different grades that have a wide range of properties and application requirements. Rare earth magnets are available in sintered as well as in bonded form.

Ceramic magnets are sintered permanent magnets composed of Barium Ferrite (BaO (Fe$_2$O$_3$)$_n$) or Strontium Ferrite (SnO(Fe$_2$O$_3$)$_n$), where n is a variable quantity of ferrite. Also known as anisotropic hexaferrites, this class of magnets is useful due to its good resistance to demagnetization and its low cost. While ceramic magnets tend to be hard and brittle, requiring special machining techniques, these magnets can be used in magnetic holding devices having very precise specifications or may be positioned within a protective cover, e.g., a plastic cover. Anisotropic grades are oriented during manufacturing, and must be magnetized in a specified direction. Ceramic magnets may also be isotropic, and are often more convenient due to their lower cost. Ceramic magnets are useful in a wide range of applications and can be pre-capped or formed for use with the present invention.

In traditional forms of laparoscopic and endoscopic surgery, laparoscopic and endoscopic instruments inserted into a body cavity or hollow viscus are manipulated principally by the application of force to the portion of the laparoscopic and endoscopic instrument protruding from the patient and integral with a handle. The handle is controlled by the surgeon and/or endoscopist and requires at all times the instrument body being placed through a trocar or other insertion orifice. Although this method is useful for adjusting the depth of insertion of the laparoscopic and NOTES instrument and can provide a limited range of angular or side-to-side movement, all but minor changes in the orientation of conventional laparoscopic and NOTES instrument may be accomplished without the creation of additional incisions in the patient.

The laparoscopic and NOTES surgical device of the present invention serves as a general-purpose platform to which a variety of surgical devices can be attached, controlled and positioned independently by the surgeon. Depending on the size, shape and type of laparoscopic and NOTES surgical device a variety of surgical methods may be used including insertion through an incision and or a trocar. In particular, the NOTES surgical devices may be introduced via a natural orifice (e.g., mouth, anus, vagina, etc) and navigated to a suitable location therein.

Laparoscopic and NOTES surgical devices that are inserted through the trocar or overtube are constrained to the size of the access port, e.g., must be collapsible to clear the minimal cross section of the access port for insertion; this is typically accomplished through pin joints which also allow for relative link motion when coupled to two external anchors. The magnetically-coupled surgical device may also be capable of self-actuation, e.g., self-actuating scissors, graspers, hook cautery, and fine-scan motion cameras. Unlike the recent generation of laparoscopic surgical robots however, the laparoscopic and NOTES surgical devices of the present invention neither require, nor are limited, by the standard working envelope of a dedicated trocar port.

The present invention provides a laparoscopic and NOTES surgical electro-cautery device body having a first side and a second side. The first side includes an anchoring and positioning mechanism and the second side includes an electro-cautery surgical mechanism. Generally, disposed in or about the laparoscopic and NOTES device body is an anchoring and positioning mechanism having a magnetic region and/or a ferrous region and a camera and/or a light. The electro-cautery surgical mechanism includes an electro-cautery tip positioned on a moveable extension and includes a pivot mechanism, a rotation mechanism, a flexible shaft or combination thereof. A magnet or ferrous material is positioned externally from the electro-cautery surgical device that is within a body cavity or hollow viscus, wherein manipulation of the magnet directs movement of the device within the body cavity or hollow viscus.

The present invention also provides a laparoscopic and NOTES surgical retention, clamp or "gripper" device. The laparoscopic and NOTES surgical retention device includes a device body having a first side and a second side. The first side includes an anchoring and positioning mechanism and the second side including a retention device having one or more movable members. The one or more movable members are used to grasp an item. The retention device includes a moveable extension, a pivot mechanism, a rotation mechanism, a flexible shaft or combination thereof. The retention device is internally powered, externally powered, or combination thereof.

In addition, a laparoscopic and NOTES surgical needle device is provided by the present invention. The laparoscopic and NOTES device body includes a first side having an anchoring and positioning mechanism and a second side having a needle positioned in a needle driving device, wherein the needle has a lumen. The needle driving device includes a moveable extension, a pivot mechanism, a rotation mechanism, a flexible shaft or combination thereof and may be internally powered, externally powered, or combination thereof. The device also includes an insertion rod moveably positioned in the lumen, wherein the insertion rod extends through the hole created by the needle and into the interior of the opening.

A laparoscopic and NOTES surgical vacuum cup device is also provided. The laparoscopic and NOTES surgical vacuum cup device has a first side and a second side. The first side includes an anchoring and positioning mechanism and the second side includes a vacuum cup extension on or about a telescopic arm or structure connected to a vacuum cup. The vacuum cup extension includes a pivot mechanism, a rotation mechanism, a flexible shaft or combination thereof. Generally, the vacuum cup is connected to a vacuum source.

In addition, the present invention provides a method of using the laparoscopic and NOTES surgical devices discloses herein. The laparoscopic and NOTES surgical device is positioned within a cavity or hollow viscus and secured in position. The laparoscopic and NOTES surgical device is then activated. The laparoscopic and NOTES surgical device may be a laparoscopic and NOTES electro-cautery surgical device, a laparoscopic and NOTES surgical retention device, a laparoscopic and NOTES surgical needle device, a laparoscopic and NOTES surgical vacuum cup device or a combination thereof.

FIG. 1 is an isometric view of one embodiment of the laparoscopic and NOTES cautery device 10 of the present invention and includes two pad openings 12 in relation on top surface 14. In this figure, the two pad openings 12 do not extent through the top surface 14; however, other embodiments may include pad openings 12 that extent through the top surface 14. In addition, pad openings 12 may vary in number (e.g., 1, 3, 4, 5, 6, 7, 8, 9, 10 or more), size/shape (e.g., linear, parallel, square, oval, round or combinations thereof) and location in the top surface 14, side surface 16 or bottom surface (not shown). The laparoscopic and NOTES cautery device 10 includes a pivotable lever 18 connected to the cautery unit 20 having a cautery tip 22.

While depicted as pad openings 12, the pad openings 12 are provided to add, when required, one or more mechanical attachment inserts. When used with suction, the pad openings may remain as openings. Examples of inserts that may be placed in the pad openings 12 include, but are nor limited to, ferrous materials, magnetic materials, pin holders, suction cups, hook and loop structures, hooks, one or more pins, retractable attachments (hooks, pins and combinations thereof), hydrophilic materials, hydrophobic materials, beads, reservoirs, gel-like materials, a mechanical trap (e.g., a biaxial locking mechanism), and combinations thereof.

In certain embodiments, magnets may be placed in the pad openings 12 to secure or move or position the laparoscopic and NOTES devices. The magnets may be permanent magnets generating a magnetic field of a constant strength. In other embodiments, the magnetic field may be an electromagnetic field having a constant strength, a variable strength, or a varying time-dependent strength. Magnetic fields for use with the present invention may be single magnetic sources, or may be composed of arrays of smaller sources. In one embodiment, the pads are magnetic pads that are attracted to a ferrous material external to the lumen, e.g., a single attachment point on a stand, a wire or even a three-dimensional cover that is positioned over the surgical subject or patient. In another embodiment, the pads are ferrous materials that are attracted to a magnetic material external to the lumen. In yet another embodiment, both the laparoscopic and NOTES device and the external positioning and/or attachment point are magnetic.

The laparoscopic and NOTES device may be made in part or entirely of one or more materials, e.g., surgical plastic, stainless steel, aluminum, titanium, nylon, polyester or other polymeric materials, alloys, and mixtures and combinations thereof. The components of the present invention may be made of a unitary construction using, e.g., molding, milling and the like. With any of the present inventions the laparoscopic and NOTES device body may be of any shape (e.g., spherical, rectangular, cubical, freeform) or dimension desired and not limited to the specific shape or structure disclosed herein. Furthermore, the device may be coated with or deliver active agents to a specific location, e.g., anti-microbial, anti-inflammatory, pain reducing or numbing agents.

Figure 2:
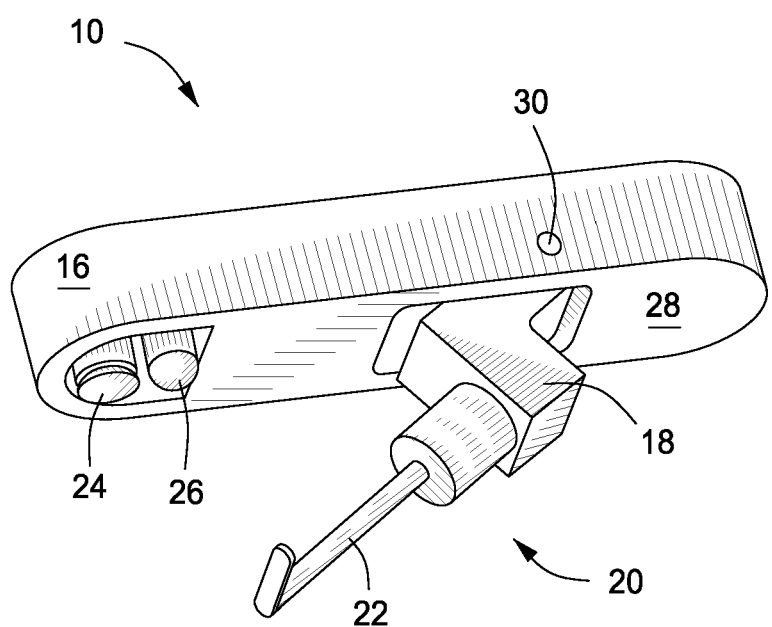
FIG. 2 is another isometric view of the laparoscopic and NOTES electro-cautery surgical device of the present invention.

FIG. 2 is another isometric view of one embodiment of the laparoscopic and NOTES cautery device 10 of the present invention illustrating a camera 24 and a illumine device 26 in relation on the bottom surface 28 and the side surface 16. The laparoscopic and NOTES cautery device 10 includes a pivotable lever 18 extending from the bottom surface 28 and connected to the cautery tip 22. The pivotable lever 18 may pivot about the axel 30 to position the cautery tip 22 for cauterization. This positioning may be aided by the use of the camera 24 and the illumine device 26. In addition, the laparoscopic and NOTES cautery device 10 may be connected to a power supply (not shown), an imaging device (not shown), a display (not shown), a fiber optic (not shown), control device (not shown) or combination thereof with a cable (not shown), wire (not shown), optical cable (not shown), fiber optic (not shown) or combination thereof. In addition, the laparoscopic and NOTES cautery device 10 may include internal power, external power, inductive power or a combination thereof.

Figure 3:
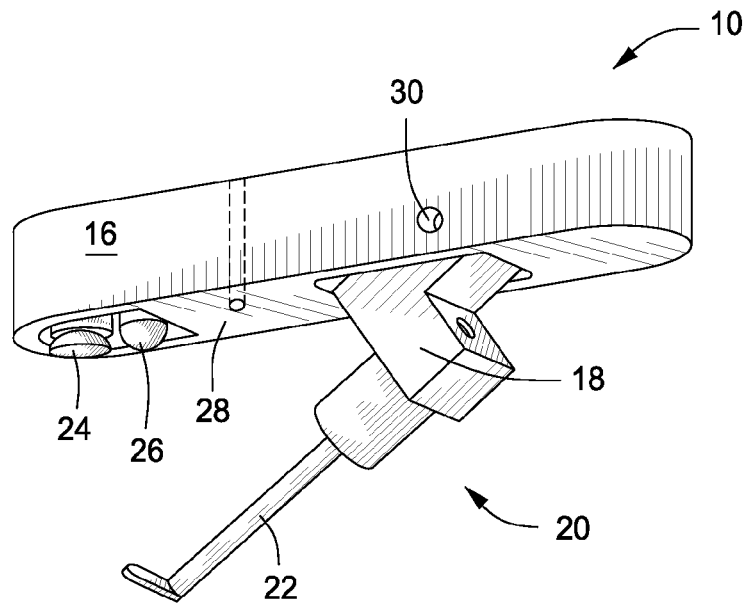
FIG. 3 is another isometric view of the laparoscopic and NOTES electro-cautery surgical device of the present invention.

FIG. 3 is another isometric view of one embodiment of the laparoscopic and NOTES cautery device 10 of the present invention. The laparoscopic and NOTES cautery device 10 includes a camera 24 and a illumine device 26 in relation on the bottom surface 28 and the side surface 16. The laparoscopic and NOTES cautery device 10 includes a pivotable lever 18 connected to cautery tip 22. The pivotable lever 18 may pivot about the axle 30 to position the cautery tip 22 for cauterization. This positioning may be aided by the use of the onboard camera 24 and the illumine device 26. In addition, the laparoscopic and NOTES cautery device 10 may be connected to a power supply (not shown), an imaging device (not shown), a display (not shown), a fiber optic (not shown), control device (not shown), a pneumatic source (not depicted) or combination thereof through a cable (not shown), wire (not shown), optical cable (not shown), fiber optic (not shown) or combination thereof. In addition, the laparoscopic cautery device 10 may include internal power, external power, inductive power or a combination thereof.

Generally, the laparoscopic and NOTES cautery device 10 is a relatively small medical instrument used for searing tissue or wounds to reduce bleeding, e.g., electrocautery. The localized temperature at the tip may reach approximately 1000° C. in some instances; however, other temperatures are also acceptable. The laparoscopic and NOTES cautery device 10 may be powered by an internal source, connected to an external source, coupled to a source that induces power or a combination thereof. The laparoscopic and NOTES cautery device 10 includes a cautery tip 22 that may be made of a variety of materials (e.g., platinum-iridium alloy), various lengths and diameters (e.g., 0.05 mm to 0.2 mm to 5 mm in diameter) and various orientations (e.g., straight tip, angled tip, etc.) known to the skilled artisan.

Figure 4:
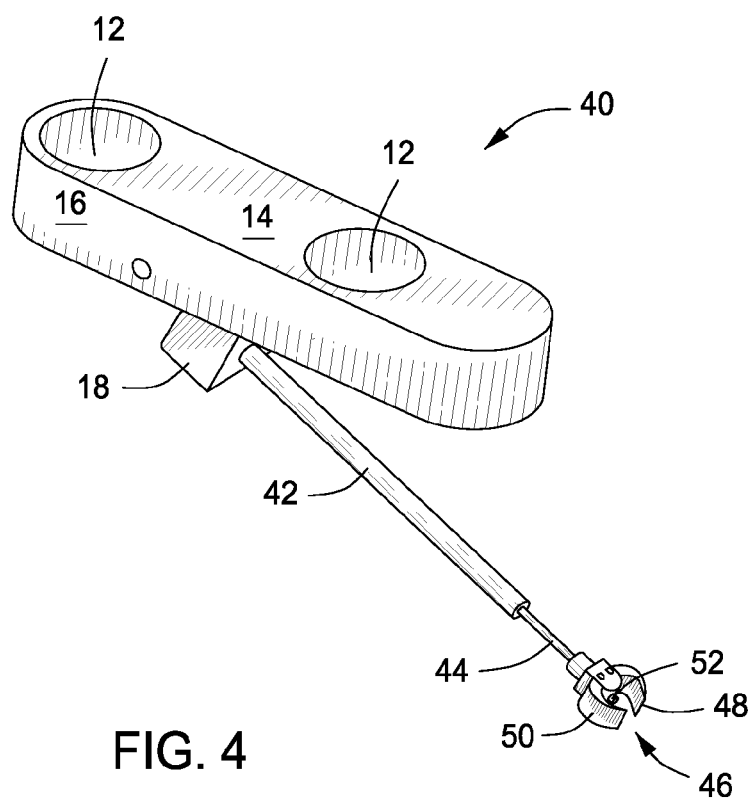
FIG. 4 is an isometric view of the laparoscopic and NOTES surgical retention device of the present invention.

FIG. 4 is an isometric view of one embodiment of the laparoscopic and NOTES surgical retention device 40 of the present invention having two pad openings 12 in relation on the top surface 14. Generally, the two pad openings 12 do not extent through the top surface 14 to the bottom surface (not shown); however, other embodiments may include pad openings 12 that extent through the top surface 14 or are tapered in shaped to frictionally fit one or more magnetic or ferrous materials (not shown) and/or vacuum plenums. In addition, pad openings 12 may vary in number (e.g., 1, 3, 4, 5, 6, 7, 8, 9, 10 or more), size/shape (e.g., linear, parallel, square, oval, round or combination thereof) and location in the top surface 14, the side surface 16 or the bottom surface (not shown). The laparoscopic and NOTES surgical retention device 40 includes a pivotable lever 18 extending from the bottom surface 28 and connected to a retention extension 42 and a moveable piston 44 that may move in and out of the retention extension 42 to extend the range of movement of the retention mechanism 46 positioned at the one end of the moveable piston 44. The retention mechanism 46 includes a first arm 48 and a second arm 50 positioned movably thereon. The first arm 48 and second arm 50 may be used to close around an object, e.g., a vein, an organ, a foreign body and so forth. In some embodiments, the retention mechanism 46 is controlled remotely by the operator; however, in other embodiments, the retention mechanism 46 is self actuating using activator 52. Upon contact with the activator 52, the first arm 48 and second arm 50 close to secure the object.

Figure 5:
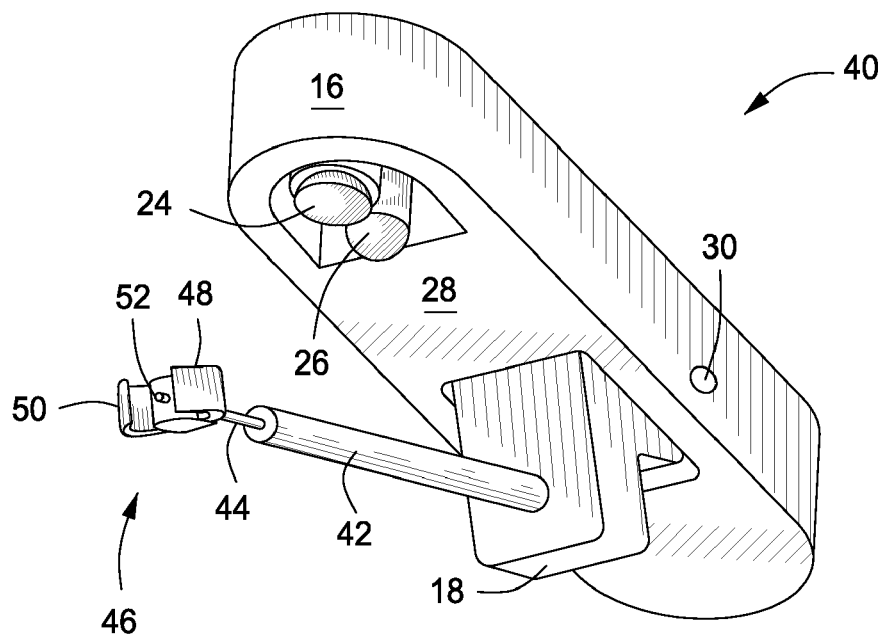
FIG. 5 is another isometric view of the laparoscopic and NOTES surgical retention device of the present invention.

FIG. 5 is isometric view of one embodiment of the laparoscopic and NOTES surgical retention device 40 of the present invention illustrating a camera 24 and an illumine device 26 in relation on the bottom surface 28 and the side surface 16. The laparoscopic and NOTES surgical retention device 40 includes a pivotable lever 18 extending from the bottom surface 28 and connected to a retention extension 42 and a telescopic structure 44 that may move in and out of the retention extension 42 to extend the range of movement of the retention mechanism 46 positioned at one end of the moveable telescopic structure 44. The retention mechanism 46 includes a first arm 48 and a second arm 50 movably positioned thereon. The first arm 48 and second arm 50 may be used to close around an object, e.g., a vein, an organ, a foreign body and so forth. In some embodiments, the retention mechanism 46 is self-actuating using activator 52. Upon contact with the activator 52 the first arm 48 and second arm 50 are closed to secure the object. The positioning of the retention mechanism 46 may be aided by the camera 24 and the illumine device 26. In addition, the laparoscopic and NOTES surgical retention device 40 may be connected to a power supply (not shown), an imaging device (not shown), a display (not shown), a fiber optic (not shown), control device (not shown) or combination thereof with a cable (not shown), wire (not shown), optical cable (not shown), fiber optic (not shown), a pneumatic source (not depicted) or combination thereof. In addition, the laparoscopic and NOTES surgical retention device 40 may include internal power, external power connection, inductive power or a combination thereof.

Figure 6:
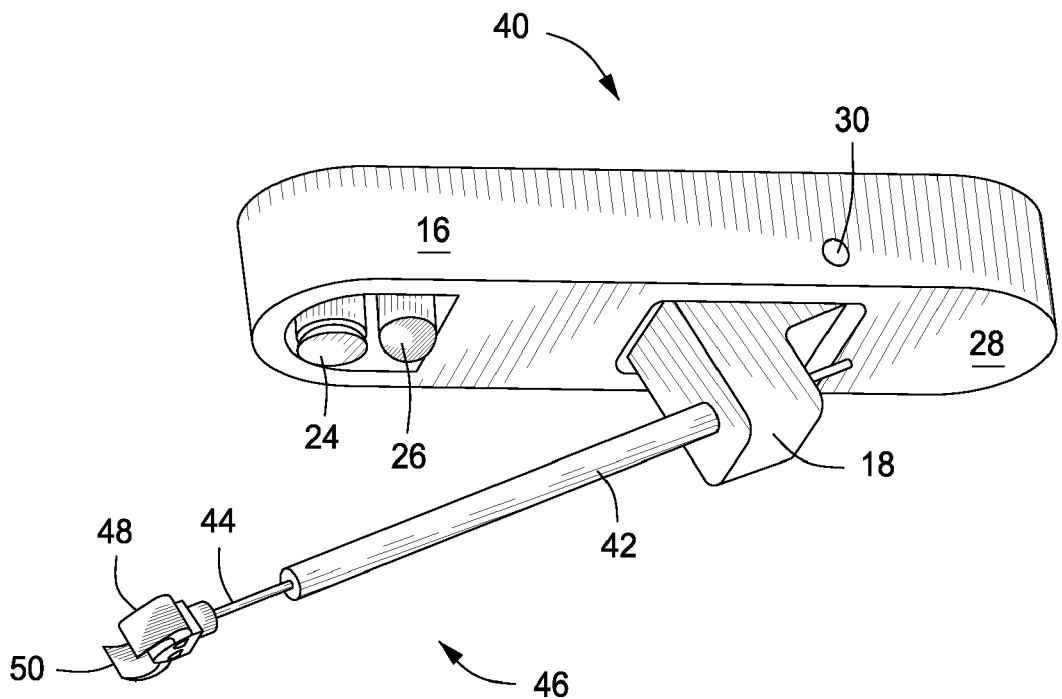
FIG. 6 is another isometric view of the laparoscopic and NOTES surgical retention device of the present invention.

FIG. 6 is another isometric view of one embodiment of the laparoscopic and NOTES surgical retention device 40 of the present invention illustrating a camera 24 and a illumine device 26 in relation on the bottom surface 28 and the side surface 16. The laparoscopic surgical retention device 40 includes a pivotable lever 18 connected to a retention mechanism 46. The pivotable lever 18 may pivot about the axle 30 to position the retention mechanism 46 at the proper position to secured or retract an object. The retention mechanism 46 includes a retention extension 42 and a moveable piston 44 to extend the range of movement. The retention mechanism 46 includes a first arm 48 and a second arm 50 movably positioned thereon to close around an object, e.g., a vein, an organ, a foreign body and so forth. In some embodiments, the retention mechanism 46 is self-actuating using activator 52. Upon contact with the activator 52 the first arm 48 and second arm 50 close to secure the object.

The retention extension 42 and moveable telescopic structure 44 are configured to move and provide extension of the retention mechanism 46. The mechanism that causes the retention extension 42 and moveable telescopic structure 44 to retract or extend may be any mechanism known in the art. For example, the retention extension 42 can be used to position the retention mechanism 46 to the desired location by the moveable telescopic structure 44 to extend/retract the retention mechanism 46. In some instances, the mechanism is moved by pneumatic power (e.g., pneumatic piston), an electric motor, a gear mechanism and similar devices known to the skilled artisan. In addition to extending/retracting, the mechanism may pivot or rotate independently. Furthermore, the retention extension 42 and or the moveable telescopic structure 44 may be flexible, e.g., polymer, spring, wire, filament, elastic or other material known to the skilled artisan.

The first arm 48 and second arm 50 may be closed by a mechanical or pneumatic source that directly moves the first arm 48 and second arm 50 together. In other embodiments, the source that moves the first arm 48 and second arm 50 is mechanical electrical, hydraulic or other known source of power. In some embodiments, the first arm 48 and second arm 50 are closed by a mechanical activator 52 or an optical trigger. It is not necessary that both arms move as the movement of a single arm may grasp on object against a stationary arm. The number of arms (e.g., 2, 3, 4, 5, 6 or more) may be varied depending on the application. In addition, the first arm 48 and second arm 50 may be of similar or different lengths, widths, diameters, shapes, materials and so forth. In some, instances, the retention mechanism 46 may be a clamp, a retractor or a combination thereof, e.g., 2 arms to function as a retractor and 2 arms to clamp.

Figure 7:
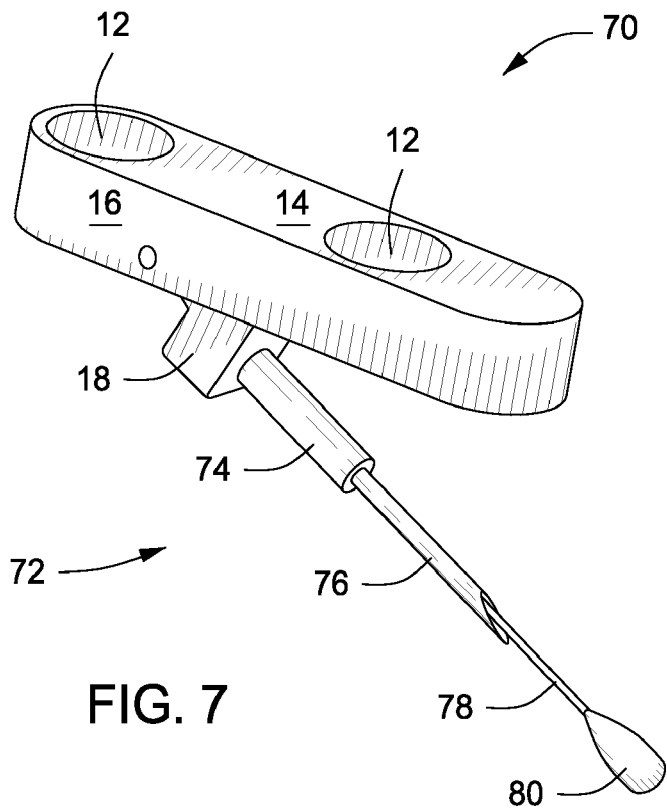
FIG. 7 is an isometric view of the laparoscopic and NOTES surgical needle device of the present invention.

FIG. 7 is an isometric view of one embodiment of the laparoscopic and NOTES surgical needle device 70 of the present invention illustrating two pad openings 12 in relation on the top surface 14. Generally, the two pad openings 12 do not extent through the top surface 14 to the bottom surface (not shown); however, other embodiments may include pad openings 12 that do extent through the top surface 14 or are tapered in shape to frictionally fit magnetic and/or ferrous materials (not shown) and/or vacuum plenums. In addition, the pad openings 12 may vary in number (e.g., 1, 3, 4, 5, 6, 7, 8, 9, 10 or more), size/shape (e.g., linear, parallel, square, oval, round or combination thereof) and location (e.g., the top surface 14, the side surface 16 or the bottom surface). The laparoscopic and NOTES surgical retention device 40 includes a pivotable lever 18 extending from the bottom surface (not shown) and connected to a piercing mechanism 72. The piercing mechanism 72 includes a driving mechanism 74 which can extend and retract a needle 76. The needle 76 may be solid, hollow or include an insertion rod 78 which may be extended through the needle lumen and hole created by the needle 76. In some embodiments, an object may be connected to the insertion rod 78 for insertion into the interior of the opening, e.g., a balloon (80), t-fastener, clip (not shown) or fish-hook shaped device (not shown) and the needle 76 retracted.

Figure 8:
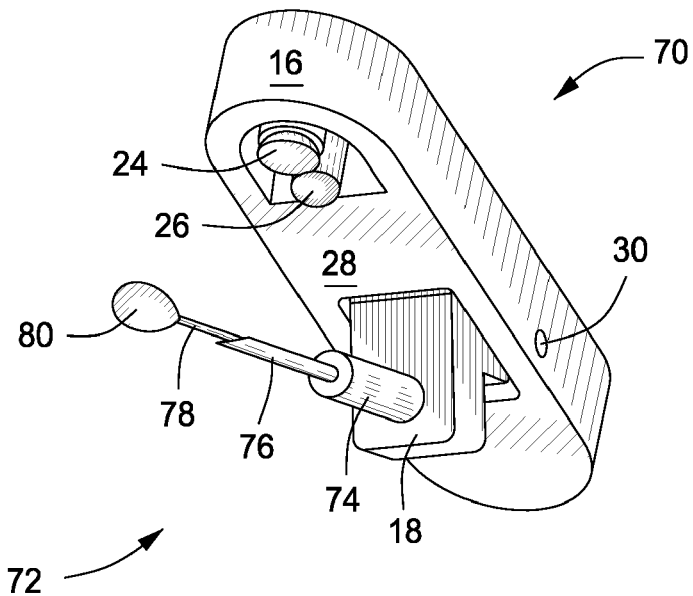
FIG. 8 is another isometric view of the laparoscopic and NOTES surgical needle device of the present invention.

FIG. 8 is isometric view of one embodiment of the laparoscopic and NOTES surgical needle device 70 of the present invention showing a camera 24 and a illumine device 26 in relation on bottom surface 28 and side surface 16. The laparoscopic and NOTES surgical needle device 70 includes a pivotable lever 18 extending from the bottom surface 28 and connecting to a piercing mechanism 72 that includes a driving mechanism 74, which can extend and retract a needle 76. The needle 76 may be solid, hollow or include an insertion rod 78 which may be extended through the hole created by the needle 76 into the interior of the opening. In some embodiments, an object may be connected to the insertion rod 78 and inserted into the opening, e.g., a balloon (80), t-fastener, clip (not shown) or fish-hook shaped device (not shown) is advanced into the organ and then the needle 76 is retracted. The positioning of the retention mechanism 46 may be aided by the use of the camera 24 and the illumine device 26. In addition, the laparoscopic and NOTES surgical needle device 70 may be connected to a power supply (not shown), an imaging device (not shown), a display (not shown), a fiber optic (not shown), control device (not shown) or combination thereof through a cable (not shown), wire (not shown), optical cable (not shown), fiber optic (not shown), a pneumatic source (not depicted) or combination thereof. In addition, the laparoscopic and NOTES surgical needle device 70 may include internal power, external power connection, inductive power or a combination thereof.

Figure 9:
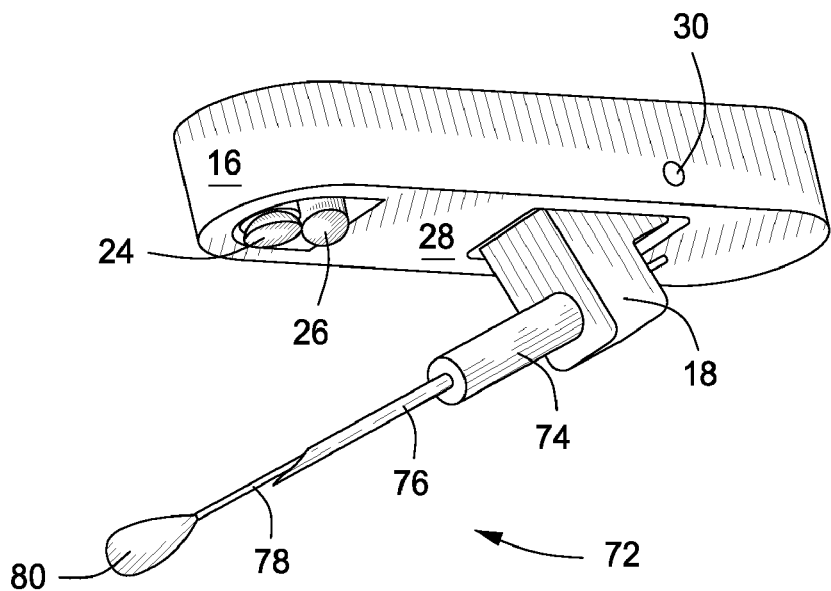
FIG. 9 is another isometric view of the laparoscopic and NOTES surgical needle device of the present invention.

FIG. 9 is another isometric view of one embodiment of the laparoscopic and NOTES surgical needle device 70 of the present invention with a camera 24 and a illumine device 26 in relation on the bottom surface 28 and the side surface 16. The laparoscopic and NOTES surgical needle device 70 includes a pivotable lever 18 connected to a piercing mechanism 72 that includes a driving mechanism 74, which can extend and retract the needle 76. The needle 76 may be solid, hollow or include an insertion rod 78 which may be extended through the hole created by the needle 76 and into the opening. In some embodiments an object may be connected to the insertion rod 78 and inserted into the opening, e.g., a balloon (80), t-fastener, clip (not shown) or fish-hook shaped device (not shown) is advanced into the organ and then the needle 76 is retracted.

The driving mechanism 74 that slides or extends the needle 76 may be any mechanism known in the art. For example, the driving mechanism 74 can also be used to position the needle 76 to the desired location. The piercing mechanism 72 may be as simple as a spring-loaded mechanism, a pneumatic mechanism (e.g., pneumatic piston), an electric motor, a gear mechanism and similar devices known to the skilled artisan that can be used to extend the needle 76 into a tissue.

The needle 76 may be expelled from the driving mechanism 74 and the insertion rod 78 may pass through the needle 76 and through the puncture. The insertion rod 78 may be extended through a simple spring-loaded mechanism, a pneumatic mechanism (e.g., pneumatic piston), an electric motor, a gear mechanism and similar devices known to the skilled artisan that can be used to extend the insertion rod 78 into the aperture created by the needle 76.

Figure 10:
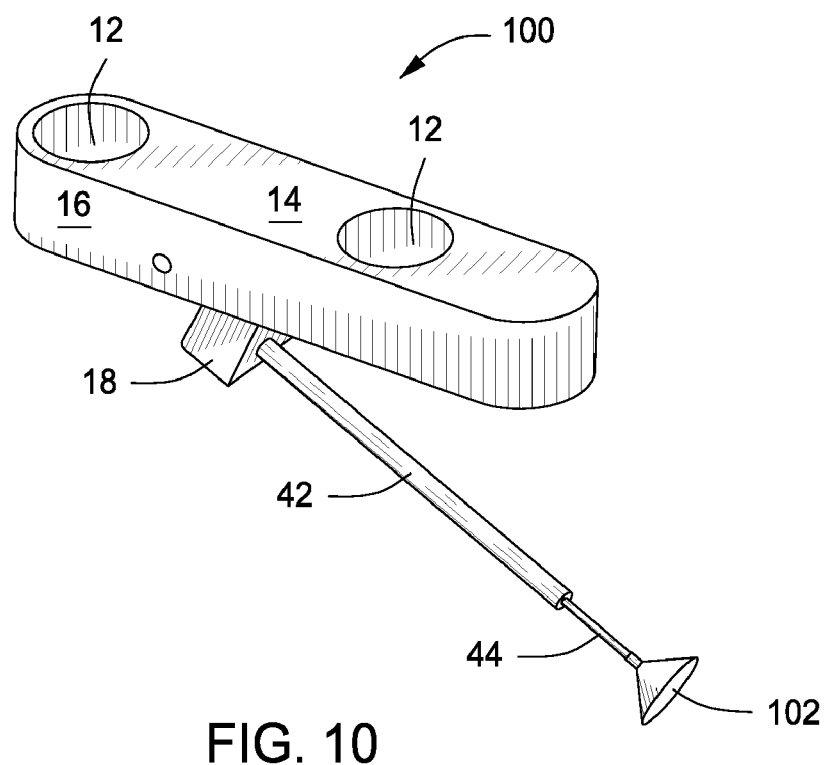
FIG. 10 is an isometric view of the laparoscopic and NOTES surgical vacuum cup device of the present invention.

FIG. 10 is an isometric view of one embodiment of the laparoscopic and NOTES vacuum cup device 100 of the present invention. The laparoscopic and NOTES vacuum cup device 100 includes two pad openings 12 in relation on top surface 14. Generally, the two pad openings 12 do not extent through the top surface 14 to the bottom surface (not shown); however, other embodiments may include pad openings 12 that do extent through the top surface 14 or are tapered in shape to frictionally fit magnetic and/or ferrous materials (not shown) and/or vacuum plenums. In addition, the pad openings 12 may vary in number (e.g., 1, 3, 4, 5, 6, 7, 8, 9, 10 or more), size/shape (e.g., linear, parallel, square, oval, round or combination thereof) and location in the top surface 14, the side surface 16 or the bottom surface (not shown). The laparoscopic vacuum cup device 100 includes a pivotable lever 18 extending from the bottom surface (not shown) and connected to a vacuum cup extension 42 and the moveable telescopic structure 44 that may move into and out of the vacuum cup extension 42 to extend the range of movement of the vacuum cup 102 positioned at the one end of the moveable telescopic structure 44. The vacuum cup 102 is positioned against/on or near an object, e.g., vein, organ, foreign body and so forth. The vacuum is applied to the vacuum cup 102 to attach thereto or to remove fluids, solids or combinations thereof. In some embodiments, the vacuum is applied by an external source; however, in other embodiments the vacuum is applied by an internal source. The positioning of the vacuum cup 102 may be aided by the use of the camera 24 and the illumine device 26. In addition, the laparoscopic vacuum cup device 100 may be connected to a power supply (not shown), an imaging device (not shown), a display (not shown), a fiber optic (not shown), control device (not shown) or combination thereof through a cable (not shown), wire (not shown), optical cable (not shown), fiber optic (not shown), a pneumatic source (not depicted) or combination thereof. In addition, the laparoscopic and NOTES surgical retention device 40 may include internal power, external power connection, inductive power or a combination thereof.

Figure 11:
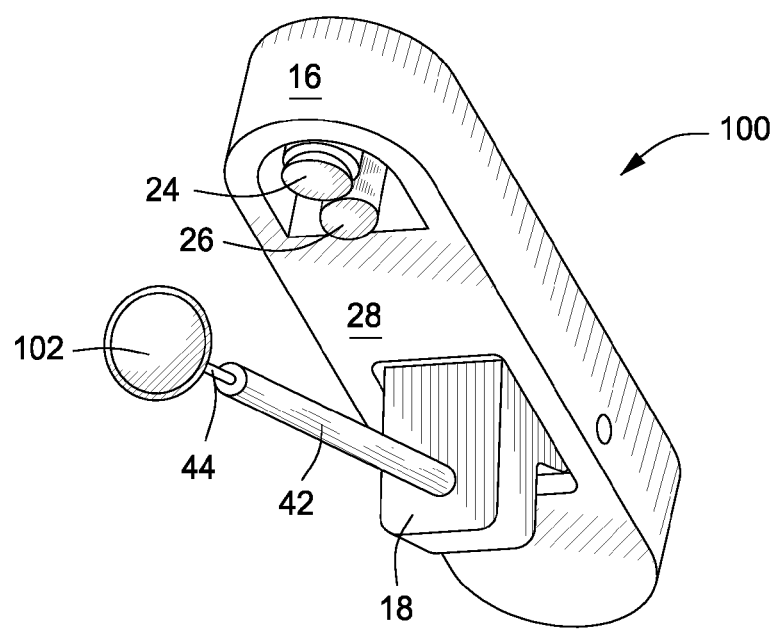
FIG. 11 is another isometric view of the laparoscopic and NOTES surgical vacuum cup device of the present invention.

FIG. 11 is isometric view of one embodiment of the laparoscopic and NOTES vacuum cup device 100 of the present invention illustrates a camera 24 and a illumine device 26 in relation on bottom surface 28 and side surface 16. The laparoscopic and NOTES vacuum cup device 100 includes a pivotable lever 18 extending from the bottom surface 28 and connected to a vacuum cup extension 42 and moveable piston 44 that may move into and out of the vacuum cup extension 42 to extend the range of movement of the vacuum cup 102 positioned at the one end of the moveable telescopic structure 44. The vacuum cup 102 is positioned against/on or near an object, e.g., vein, organ, foreign body and so forth. The vacuum is applied to the vacuum cup 102 to attach thereto or to remove fluids, solids or combinations thereof. In addition, the laparoscopic and NOTES vacuum cup device 100 may be connected to a power supply (not shown), an imaging device (not shown), a display (not shown), a fiber optic (not shown), control device (not shown) or combination thereof through a cable (not shown), wire (not shown), optical cable (not shown), fiber optic (not shown), a pneumatic source (not depicted) or combination thereof. In addition, the laparoscopic and NOTES vacuum cup device 100 may include internal power, external power connection, inductive power or a combination thereof.

Figure 12:
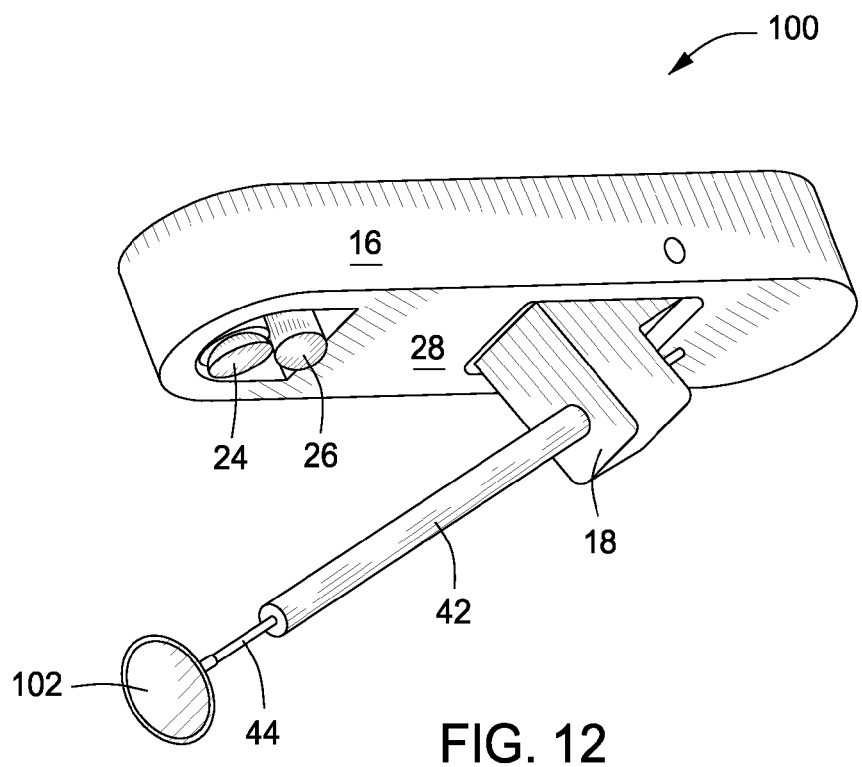
FIG. 12 is another isometric view of the laparoscopic and NOTES surgical vacuum cup device of the present invention.

FIG. 12 is another isometric view of one embodiment of the laparoscopic and NOTES vacuum cup device 100 of the present invention and includes a camera 24 and a illumine device 26 in relation on bottom surface 28 and side surface 16. The laparoscopic and NOTES vacuum cup device 100 includes a pivotable lever 18 connected to a vacuum cup extension 42 and moveable piston 44 that may move in and out of the vacuum cup extension 42 to extend the range of movement of the vacuum cup 102 that is positioned at the end of the moveable telescopic structure 44. The vacuum cup 102 may be positioned against/on or near an object, e.g., vein, organ, foreign body and so forth.

In some embodiments, the laparoscopic and NOTES device of the present invention includes two types of locking mechanisms for the pin having a pin lock, such as that disclosed by the present inventors in U.S. Patent Application US20050165449A1, relevant portions incorporated herein by reference. Briefly, the pin may have a sharpened point for traversing a tissue. To hold the pin in place, a pin lock, in this embodiment a shaft and a lock pad are included. The laparoscopic and NOTES device includes an opening having a conical focal point at the bottom of the opening through which the pin is inserted to anchor the laparoscopic and NOTES device and having a locking arm that self-locks. The pin may have serrations, which may be used to increase friction and thereby improve the anchoring capacity of the laparoscopic and NOTES device. Another variation of the locking mechanism for the pin and laparoscopic and NOTES device is one in which the serrations thread into an internal thread. When using the laparoscopic and NOTES device, the position of the laparoscopic and NOTES device as the anchor site and then may lock the anchor into position semi-permanently by inserting the pin into the self-locking mechanism.

In addition, the laparoscopic and NOTES devices of the present invention may include one or more pad openings 12 on the top surface 14. As will be apparent from the current disclosure, additional openings and pad openings 12 may be added and positioned in a linear, parallel, square, oval, round, and/or in two and three-dimensions. In addition, the size and dimensions of the pad openings 12 may vary depending on the application. In fact, some embodiments may not have pad openings 12 at all, as the materials are incorporated into the laparoscopic and NOTES device itself. Alternatively, the laparoscopic and NOTES devices may be attached to larger structures that are secured or may be secured with suction cups or pins. Thus allowing the laparoscopic and NOTES devices to be positioned by manual manipulation, or may be positioned with the help of, e.g., a magnetic field.

The pivotable lever 18 is pivotably positioned in or about the laparoscopic and NOTES devices so that the pivotable lever 18 may be moved to the desired position. The pivotable lever 18 may include attachments for manual, pneumatic, hydraulic, mechanical, electrical or other systems (including combinations thereof) to power the devices of the laparoscopic and NOTES device. In addition, the pivotable lever 18 may include attachment mechanisms for different devices.

In one specific example, the laparoscopic and NOTES device of the present invention includes an anchoring mechanism to the abdominal lumen and includes a high-resolution charge-coupled device (CCD), complementary metal oxide conductor (CMOS) camera or even an analog camera. The camera may be internally powered or externally powered. While the camera may obtain and transmit a signal independent of an external power source, the surgical anchor of the present invention may also provide electrical and optical contacts with the surgical tool attached to the surgical anchor. For example, a camera and light may obtain, e.g., electrical power from the pin and be grounded via the patient or a wire or pin. The wire or pin may be made of, or includes, optic fiber, a signal may be transmitted to and from the camera through the pin or the cable itself. The pin or the cable may even provide electrical, mechanical, pneumatic, communications and the like to the surgical tool via or around the surgical anchor and NOTES platform. In another embodiment, the camera delivers a signal via a radio frequency or other transmission system and is wireless.

The sensitivity, reliability and simplicity of operation of the system may be evaluated by direct comparison to conventional images captured using conventional laparoscopic and endoscopic instruments. Other image capture systems may be used in conjunction with the imaging system. For example, fiber optic leads may be placed close to the image and the image transferred for capture outside the body. In addition, wavelengths outside visible light may be captured by the imaging system.

Typically, an illuminating device 26 is required for a video system to transmit a signal for use in surgery. The cable may include additional wires, optical fiber and pneumatic lines into, e.g., the abdominal area to provide command, control and electrical connections through the abdominal wall or hollow viscus without leaking gas out of the abdomen. The trocar cable and light port has one or more internal conduits that traverse the length of the trocar cable and light port and through which one or more cables, optic fiber and pneumatic lines may be inserted into the patient, while at the same time maintaining access to the intraabdominal cavity and hollow viscus through the trocar and NOTES platform.

Figure 13A:
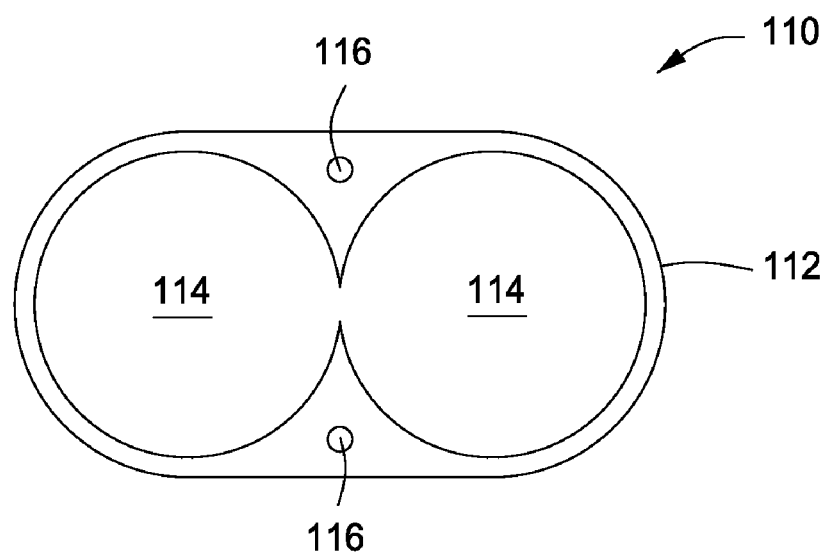
FIGS. 13A and 13B are view of a dual external magnet stack in top view and cross-sectional view respectively.
Figure 13B:
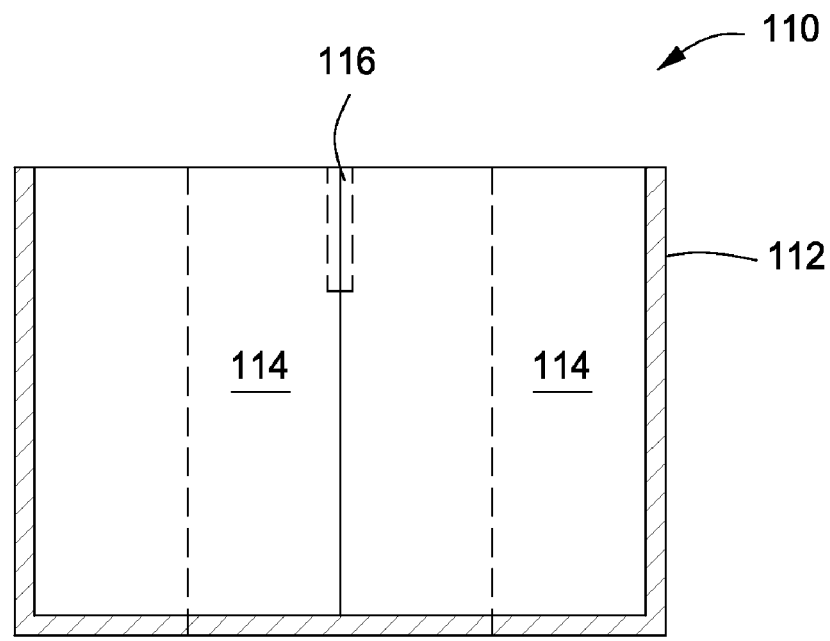

FIG. 13A is a top view of a dual-magnet and FIG. 13B is cross-sectional view of the dual magnet stack 110 for use with any of the laparoscopic and NOTES devices of the present invention made of, or including, a magnetically attracting material. The dual external magnet stack 110 has a casing 112 having one or more magnet holding openings 114 that generally will be small enough to be hand-held. Into each of the magnet holding openings 114 may be inserted a magnetic source in: N-S, S-N, S-S or N-N orientation. In one embodiment, the magnet is an electromagnet and the strength and orientation of the field may be externally controlled by providing power to the electromagnet. The magnet holding openings 114 are depicted as cylindrical, however, they may have any shape: oval, square, rectangular, etc. The holes 116 in the casing 112 and may be used to attach the dual external magnet stack 110 to a stand or holder. One particularly useful aspect of the dual external magnet stack 110 is that, when used in conjunction with the laparoscopic and NOTES surgical device 10 depicted in FIG. 1 having pads (not shown) included into pad openings 12 in the top surface 14. The dual external magnet stack 110 may be used to turn the laparoscopic surgical device 10 about a range of 360 degrees, while magnetically coupling the each of the magnets of the dual stack to one of the pads (not shown).

Figure 14:
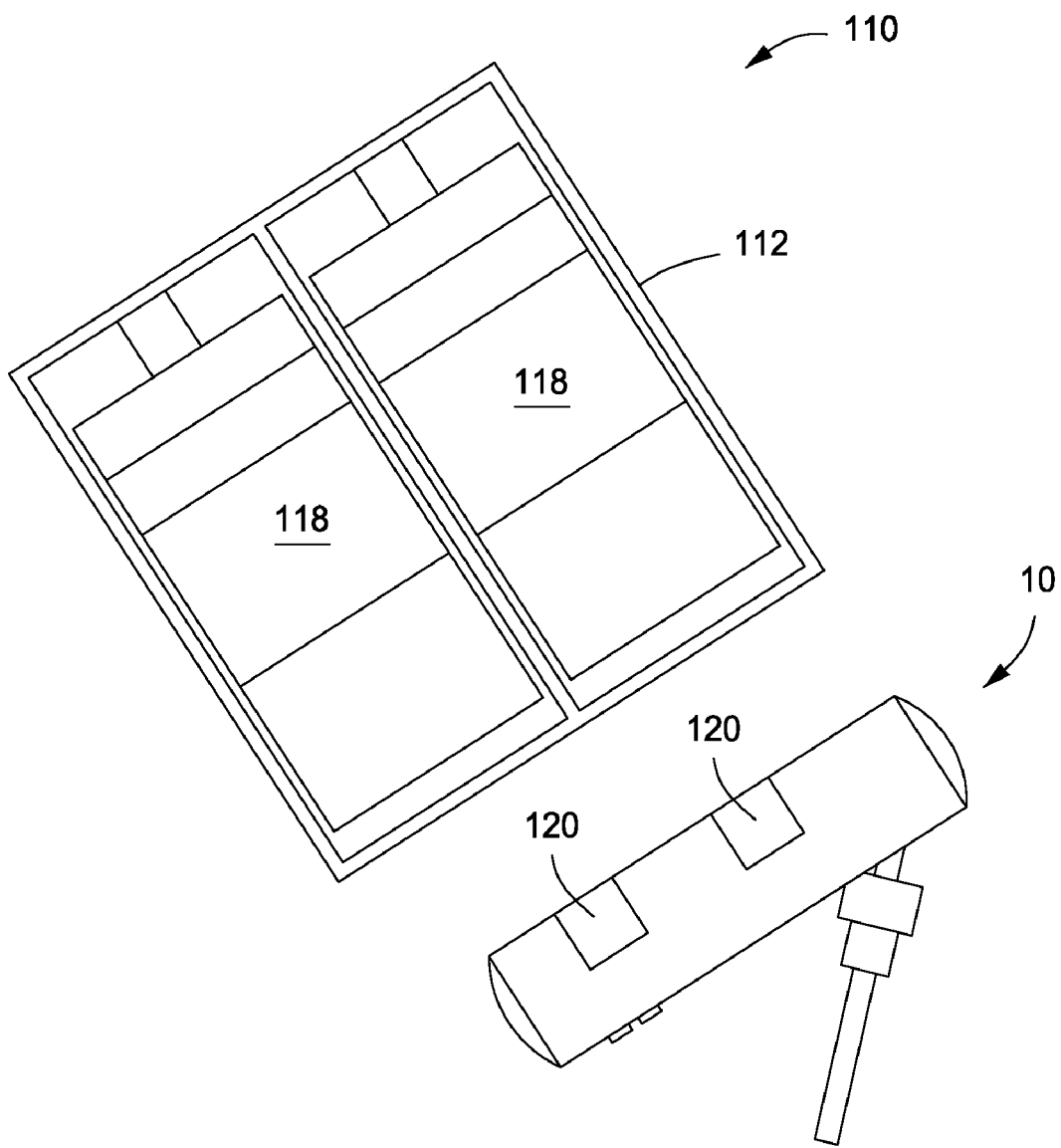
FIG. 14 is a cross-sectional view combining the laparoscopic and NOTES surgical device and the dual external magnet stack for use with the present invention.

FIG. 14 is a cross-sectional view combining the laparoscopic and NOTES surgical device 10 and the dual external magnet stack 110 for use with the present invention. FIG. 14 combines the dual external magnet stack 110 having magnets 118 in the casing 112 with a laparoscopic and NOTES surgical device 10. The laparoscopic and NOTES surgical device 10 is also shown in cross-section and with the pad openings 12 containing the pads 120 that are of a magnetically attracting material. By using the combination of the dual external magnet stack 110 with the pads 120 that are of a magnetically attracting material, the laparoscopic surgical device 10 may be rotated 360 degrees under the external control of the surgeon by rotating the dual external magnet stack 110.

The laparoscopic and NOTES device of the present invention provides several distinct advantages over the use of conventional hand-held laparoscopic and endoscopic tools. First, it provides an independent anchor point for the attachment of one or more surgical tools, retractors, clamps, scalpels, cameras, lights and the like that are inserted once into the patient through a single trocar or natural orifice. The laparoscopic and NOTES device may be anchored to the lumen of the body cavity or hollow viscus using external magnets or by insertion of a single small pin, which may attached via, e.g., a self-locking mechanism, thereby providing a hands-free anchor point for other tools while also freeing-up the trocar for insertion of additional anchors of providing for insertion of another working surgical tool. Second, one or more independent tools may be swapped between the anchors to increase the functionality and flexibility of the system. Third, by using magnetic positioning, the same surgical anchor may be moved from location to location, again reducing the number of major incisions while allowing maximum flexibility for tool use and positioning.

The laparoscopic and NOTES device for use with the present invention will generally be sized to be passable through an incision or a trocar port by a laparoscopic and NOTES grasper or forceps for attachment to the surgical anchor. In some cases, it may be desirable for the laparoscopic and NOTES device to be a camera, a camera with one or more lights (e.g., optic fibers), surgical retractors, e.g., a retractor, a sling retractor, a paddle retractor, a clamp, a basket, a bag, a hook and the like, a cutting tool, e.g., a laser or a scalpel, or even a suction tube for removal of tissue. The laparoscopic and NOTES device may include a hook or other locking mechanism that is complementary with an anchor point. The laparoscopic and NOTES device may be formed of metal, plastic, combination of metal and plastics or other suitable material. The surgical tool may also include drawstrings to help remove the surgical tool through the trocar or other opening after use.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A surgical electro-cautery device comprising:
a device body;
a first magnetic or ferrous material in a first portion of the device body;
a second magnetic or ferrous material in a second portion of the device body, the first and second portions of the device body being spaced apart from each other; and
an electro-cautery surgical mechanism coupled to the device body, the electro-cautery surgical mechanism including a rotation mechanism.

2. The device of claim 1, wherein the device body further comprises, a suction region.

3. The device of claim 1, further comprising a camera, a light or combination thereof disposed in or about the device body.

4. The device of claim 1, wherein the electro-cautery surgical mechanism comprises a straight electro-cautery tip positioned on a moveable extension.

5. The device of claim 1, wherein the electro-cautery surgical mechanism comprises a flexible shaft.

6. The device of claim 1, wherein the electro-cautery surgical mechanism is internally powered, externally powered, or a combination thereof.

7. The device of claim 1, wherein the electro-cautery surgical mechanism is hydraulically or pneumatically powered.

8. The device of claim 1, further comprising a drawstring for removing the device.

9. The device of claim 1, wherein the device body comprises a surgical plastic.

10. The device of claim 1, further comprising a casing comprising a first material and a second material, the first and second materials being configured and positioned to magnetically couple to the first and second magnetic or ferrous materials in the device body such that the position of the device body within a body cavity or viscus can be changed by manipulating the casing outside the body cavity or viscus.

11. A surgical electro-cautery device comprising:
a device body;
a first magnetic or ferrous material in a first portion of the device body;
a second magnetic or ferrous material in a second portion of the device body, the first and second portions of the device body being spaced apart from each other; and
an electro-cautery surgical mechanism coupled to the device body, the electro-cautery surgical mechanism having a straight electro-cautery tip.

12. The device of claim 11, further comprising a casing comprising a first material and a second material, the first and second materials being configured and positioned to magnetically couple to the first and second magnetic or ferrous materials in the device body such that the position of the device body within a body cavity or viscus can be changed by manipulating the casing outside the body cavity or viscus.

13. The device of claim 11, further comprising a camera, a light or combination thereof disposed in or about the device body.

14. The device of claim 11, wherein the electro-cautery surgical mechanism comprises a flexible shaft.

15. The device of claim 11, wherein the electro-cautery surgical mechanism is internally powered, externally powered, or a combination thereof.

16. The device of claim 11, wherein the electro-cautery surgical mechanism is hydraulically or pneumatically powered.

17. The device of claim 11, further comprising a drawstring for removing the device.

18. The device of claim 11, wherein the device body comprises a surgical plastic.

19. A surgical electro-cautery device comprising:
a device body having a leading end a trailing end;
a first magnetic or ferrous material in a first portion of the device body;
a second magnetic or ferrous material in a second portion of the device body, the first and second portions of the device body being spaced apart from each other;

an electro-cautery surgical mechanism coupled to the device body at a location nearer the trailing end than the leading end; and a camera and a light coupled to the device body at respective locations that are nearer the leading end than the trailing end.

20. The device of claim 19, further comprising a casing comprising a first material and a second material, the first and second materials being configured and positioned to magnetically couple to the first and second magnetic or ferrous materials in the device body such that the position of the device body within a body cavity or viscus can be changed by manipulating the casing outside the body cavity or viscus.

21. The device of claim 19, wherein the electro-cautery surgical mechanism comprises a flexible shaft.

22. The device of claim 19, wherein the electro-cautery surgical mechanism is internally powered, externally powered, or a combination thereof.

23. The device of claim 19, wherein the electro-cautery surgical mechanism is hydraulically or pneumatically powered.

24. The device of claim 19, further comprising a drawstring for removing the device.

25. The device of claim 19, wherein the device body comprises a surgical plastic.

* * * * *